United States Patent [19]

Young

[11] 4,234,751
[45] Nov. 18, 1980

[54] SELECTIVE CRACKING OF PHENYLALKANES

[75] Inventor: Lewis B. Young, Skillman, N.J.

[73] Assignee: Mobil Oil Corporation, New York, N.Y.

[21] Appl. No.: 61,222

[22] Filed: Jul. 27, 1979

[51] Int. Cl.³ .................................................. C07C 4/06
[52] U.S. Cl. .................................. 585/486; 585/456; 585/488; 585/852
[58] Field of Search ............... 585/455, 456, 486, 487, 585/488, 852

[56] References Cited

U.S. PATENT DOCUMENTS

| | | | |
|---|---|---|---|
| 3,235,616 | 2/1966 | Sharman | 585/486 |
| 3,342,888 | 9/1967 | DeWitt et al. | 585/486 |
| 3,474,154 | 10/1969 | Yamanaka et al. | 585/486 |
| 3,926,782 | 12/1975 | Plank et al. | 585/486 |

Primary Examiner—C. Davis
Attorney, Agent, or Firm—Charles A. Huggett; James F. Powers; Ronald J. Cier

[57] ABSTRACT

A process for the production of the internal isomers (3-phenyl, 4-phenyl and higher) from linear phenylalkane mixtures via selective cracking of the 2-phenylalkane isomer over crystalline zeolite catalysts having a silica to alumina ratio of at least about 12 and a constraint index, as herein defined, of about 1 to 12.

14 Claims, No Drawings

SELECTIVE CRACKING OF PHENYLALKANES

BACKGROUND OF THE INVENTION

1. Field of the Invention

This invention is concerned with the production of internal isomers from linear phenylalkane mixtures via selective cracking of the 2-phenylalkane in the presence of a shape-selective zeolite catalyst.

2. Description of the Invention

Detergent alkylates comprising linear phenylalkylsulfonates are known to be useful and desirable detergents. Phenyldodecylsulfonate in particular is widely employed in the detergent industry and it is known that the location on the alkyl chain of the average phenyl group has significant effect on the detergency properties of the sulfonate. For instance, it has been demonstrated that by shifting the average phenyl group location to more internal positions one increases the solubility, wetting power and foaming power of the phenyldodecylsulfonates. Tjepkena et al., 5th *World Petroleum Congress*, Sect. 4, No. 21 (1959).

Phenyldodecylsulfonate is prepared from phenyldodecane intermediate, the position of the phenyl group in the intermediate being fixed during the initial reaction of benzene with the linear olefin. The production of the intermediate is conventionally carried out in the presence of a Friedel-Crafts catalyst (e.g. AlCl$_3$) to give a mixture of all of the possible positional isomers. Many attempts to reduce the external phenyl isomer concentration (i.e. the 2-phenylalkane), and thereby increase the relative amount of the more desirable internal isomers (the 3-phenyl, the 4-phenyl, etc.), have been reported, but only small reductions of the 2-phenyl isomer content have been achieved.

SUMMARY OF THE INVENTION

I have now discovered a process whereby the 2-phenylalkane isomer can be selectively removed from isomeric phenylalkane mixtures without significant loss of the more valuable internal isomers (3-phenyl, 4-phenyl, etc.). The phenylalkane mixture is brought into contact with a particular type of shape-selective crystalline zeolite catalyst, having appropriate pore dimensions, at a temperature and pressure conductive to the cracking reaction. Upon contact with the catalyst the 2p-phenylalkane is selectively cracked to yield benzene, olefins, and lower molecular weight alkylbenzenes, while leaving the other positional isomers substantially unreacted.

The particular shape-selective crystalline zeolite catalysts useful herein can be characterized as having a silica to alumina ratio of at least about 12 and a constraint index, as hereinafter defined, of from 1 to 12. Selective cracking is effectively accomplished at temperatures of between about 150° C. and about 550° C. and at pressures of from about $10^4$ N/m$^2$ to about $10^6$ N/m$^2$ (0.1–10 atmospheres).

DESCRIPTION OF SPECIFIC EMBODIMENTS

Mild Friedel-Crafts alkylation of benzene with linear olefins produces a mixture of linear phenylalkanes. For example, any of the linear dodecenes will produce substantially the same mixture of the five possible positional isomers of phenyldodecane (2-phenyl; 3-phenyl; 4-phenyl; 5-phenyl; 6-phenyl);

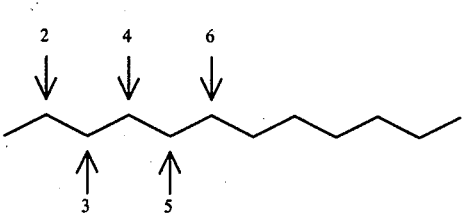

Similarly, reaction of benzene with octene is known to give a mixture of all three possible internal linear phenyloctanes:

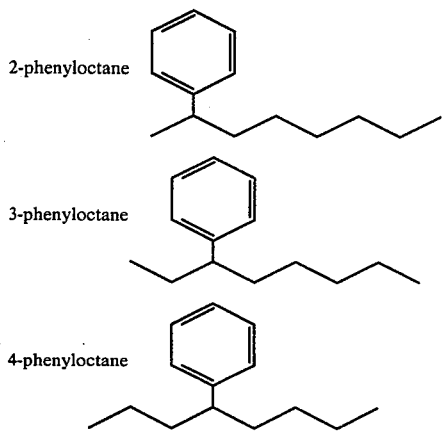

When mixtures of these linear phenyloctanes, phenyldodecanes or other similarly linear phenylalkanes are passed over the preferred crystalline zeolite catalysts defined below, highly selective cracking of the 2-isomer takes place, leaving the more internal isomers substantially unreacted and in excess of equilibrium.

The phenylalkanes with which the process of this invention may be employed are those produced as the alkylation products of benzene with linear olefinic hydrocarbons. The preferred olefins are those having from about 6 to about 20 carbon atoms in the linear chain. The alkylation reaction may desirably be carried out using conventional technology—such as the Friedel-Crafts reaction which is conducted in the presence of AlCl$_3$ or other Lewis Acid as catalyst—to produce mixtures of the various positional isomers of the phenylalkane product.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on steam between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred in some applications to use zeolites having higher silica/alumina ratios of at least about 30. In addition, zeolites as otherwise characterized herein but which are substantially free of aluminum, i.e. having silica to alumina mole ratios of 1,600 and higher, are found to be useful and even preferable in some instances. Such "high silica" zeolites are intended to be included within this description. The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of condititons within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, and other similar materials.

ZSM-5 is described in greater detail in U.S. Pat. Nos. 3,702,886 and 3,941,871. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of the catalyst, and particularly the X-ray diffraction pattern thereof, is incorporated herein by reference.

ZSM-38 is more particularly described in U.S. Pat. No. 4,046,859. The description of that catalyst, and particularly the specified X-ray diffraction pattern thereof, is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes to converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, offretite, and isotypes thereof, with ZSM-5 being particularly preferred.

In a preferred aspect of this invention, the zeolites hereof are selected as those providing among other things a crystal framework density, in the dry hydrogen form, of not less than about 1.5 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.5 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen from of the zeolite in an orgaic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.5 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume |  | Framework Density |  |
| --- | --- | --- | --- | --- |
| Ferrierite | 0.28 | cc/cc | 1.76 | g/cc |
| Mordenite | .28 |  | 1.7 |  |
| ZSM-5, -11 | .29 |  | 1.79 |  |
| ZSM-12 | — |  | 1.8 |  |
| ZSM-23 | — |  | 2.0 |  |
| Dachiardite | .32 |  | 1.72 |  |
| L | .32 |  | 1.61 |  |
| Clinoptilolite | .34 |  | 1.71 |  |
| Laumontite | .34 |  | 1.77 |  |
| ZSM-4 (Omega) | .38 |  | 1.65 |  |
| Heulandite | .39 |  | 1.69 |  |
| P | .41 |  | 1.57 |  |
| Offretite | .40 |  | 1.55 |  |
| Levynite | .40 |  | 1.54 |  |
| Erionite | .35 |  | 1.51 |  |
| Gmelinite | .44 |  | 1.46 |  |
| Chabazite | .47 |  | 1.45 |  |
| A | .5 |  | 1.3 |  |
| Y | .48 |  | 1.27 |  |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin famiies, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The preferred crystalline zeolite catalysts useful herein may desirably be modified by treatment with entails steaming of the zeolite by contact with an atmosphere containing from about 5% to about 100% steam at a temperature of from about 250° C. to about 1000° C. for a period of between about 0.25 and about 100 hours and under pressures ranging from subatmospheric to several hundred atmospheres.

Another modifying treatment involves precoking of the catalyst to deposit a coating of between about 2 and about 75, and preferably between about 15 and about 75 wt.% of coke thereon. Precoking can be accomplished by contacting the catalyst with a hydrocarbon charge, e.g. toluene, under high severity conditions or, alternatively, at a reduced hydrogen to hydrocarbon concentration (i.e. 0 to 1 mole ratio of hydrogen to hydrocarbon) for a sufficient time to deposit the desired amount of coke thereon.

The process is carried out by bringing the mixture of phenylalkanes into contact with the crystalline zeolite catalyst at conditions of temperature and pressure conductive to bringing about the cracking reaction. Temperatures of about 150° C. to 550° C. are suitable, but is is preferable that the process be carried out at between about 200° C. to about 400° C. The pressure may be from about $10^4$ N/m$^2$ to about $10^6$ N/m$^2$ (0.1–10 atmospheres) and preferably between about $5 \times 10^4$ N/m$^2$ and about $5 \times 10^5$ N/m$^2$ (0.5–5 atmospheres).

The reaction may be carried out as a batch type operation or a continuous or semi-continuous operation utilizing a fixed or moving bed catalyst system. The catalyst, after use in a moving bed reactor, may be conducted to a regeneration zone wherein coke is burned from the catalyst in an oxygen-containing atmosphere (air, for example) at elevated temperature, after which the regenerated catalyst is recycled to the conversion zone for further contact with the charge stock. In a fixed bed reactor, regeneration is carried out in a conventional manner where an inert gas containing a small amount of oxygen (e.g. 0.5–2%) is used to burn the coke in a controlled manner.

The phenylalkane mixture may be neat, i.e. devoid of diluents, when brought into contact with the catalyst or it may be diluted with other, preferably hydrocarbon, material which acts as a diluent and carrier for the phenylalkanes. A particularly preferred embodiment contemplates a phenylalkane-containing feed which is substantially the product effluent of a commercial phenylalkane production process.

Subsequent to the selective reaction of the 2-phenylalkane constituent of the phenylalkane mixture, the unreacted higher phenylalkanes (i.e., the 3-phenylalkane, 4-phenylalkane, etc.) may be recovered by conventional methods, such as distillation. The recovered higher phenylalkanes, which will be characterized by an average phenyl position on the alkyl chain substantially higher than that of the phenylalkane feed mixture, may thereafter be considered the final end-product of the process and treated accordingly. However, a preferred embodiment of the invention includes the utilization of the phenylalkane product of the selective cracking reaction in the production of improved phenylalkylsulfonates useful as superior detergent alkylates by virtue of their higher average phenyl position on the alkyl chain.

Phenylalkanes may be converted to phenylalkylsulfonates by sulfonation of the aromatic ring by sulfuric acid. The reaction is well known in the art and commonly is carried out by contacting the organic compound with sulfuric acid at temperatures of from about −7° C. to about 60° C. Detailed descriptions of specific commercial processes abound in the literature—see, for instance, pages 60–62 of *INDUSTRIAL CHEMICALS*, Third Edition, by W. L. Faith et al, published by John Wiley & Sons, Inc., 1966—and those skilled in the field will need no further instruction on how to carry out such reaction.

The following examples are presented by way of illustration so that those skilled in the art may better understand the process of this invention. They should not, however, be interpreted as placing undue limitation on the disclosed process.

EXAMPLE 1

A mixture of phenyloctanes was prepared by alkylation of benzene with a 1-octene/trans-4-octene mixture in the presence of $AlCl_3$ catalyst at a temperature and pressure of 50° C. and one atmosphere (absolute), respectively. The reaction product, comprising 11.7% 2-phenyloctane, 6.2% 3-phenyloctane, 5.0% 4-phenyloctane and 77.0% benzene, was recovered and utilized as the feed in the following selective cracking reactions.

EXAMPLE 2

The phenyloctane in benzene mixture from Example 1 was passed over 1.0 gram of HZSM-5 zeolite catayst at 350° C. and atmospheric pressure and at a feed weight hourly space velocity (WHSV) of 7. The product analysis is given in Table I below.

TABLE I

| | Feed | Product | $\phi$-$C_8$ Isomer Loss |
| --- | --- | --- | --- |
| 2-Phenyloctane | 11.7% | 0.06% | 99.5% |
| 3-Phenyloctane | 6.2% | 6.2% | } 1% |
| Benzene | 77.0% | 72.6% | |
| | — | 13.3% | |
| ⌬—R | | | |
| (R = $C_1$-$C_7$) | | | |
| Olefins | — | 2.7% | |

The 2-phenyloctane component of the feed stream has been selectively cracked to the extent of 99.5% of that present in the feed stream. However, it will be noted that only 1% of the total of the 3-phenyl plus the 4-phenyl isomers has been cracked.

EXAMPLE 3

This was a repeat of Example 2, except the HZSM-5 catalyst was steamed for 2 hours at 600° C. and 1 atmosphere pressure prior to use. The results are given in Table II.

TABLE II

| | Feed | Product | $\phi C_8$ Isomer Loss |
| --- | --- | --- | --- |
| 2-Phenyloctane | 11.7% | 0.06% | 99.5% |
| 3-Phenyloctane | 6.2% | 6.2% | } <1% |
| 4-Phenyloctane | 5.0% | 5.0% | |
| Benzene | 77.0% | | |
| | — | | |
| ⌬—R | | | |
| (R = $C_1$-$C_7$) | | | |
| Olefins | — | | |

EXAMPLE 4

The phenyloctane in benzene mixture of Example 1 was passed across 1.0 gram HZSM-12 zeolite catalyst at 275° C., 1 atmosphere of pressure and a WHSV of 44. The product analysis is given below.

TABLE III

| | Feed | Product | $\phi$-$C_8$ Isomer Loss |
| --- | --- | --- | --- |
| 2-Phenyloctane | 11.7% | 0.85% | 93% |
| 3-Phenyloctane | 6.2% | 4.9% | } 11% |
| 4-Phenyloctane | 5.0% | 5.1% | |
| Benzene | 77.0% | 80.2% | |
| | — | 4.7% | |
| ⌬—R | | | |
| (R = $C_1$-$C_7$) | | | |
| Olefins | — | 4.2% | |

EXAMPLES 5–8

Samples of Offretite, Mordenite (de-aluminized), and Beta zeolites, as well as a conventional $SiO_2.Al_2O_3$ cracking catalyst, were tested in the same manner as the foregoing examples. The results are given in Tables IV–VII.

TABLE IV

Example 5
Catalyst : Offretite
Temp. : 275° C.
Press. : Atm.
WHSV : 5

| | Feed | Product | $\phi$-$C_8$ Isomer Loss |
| --- | --- | --- | --- |
| 2-Phenyloctane | 12.5% | 1.3% | 89.6% |
| 3-Phenyloctane | 6.8% | 5.6% | 17.7% |
| 4-Phenyloctane | 5.5% | 5.5% | 0% |
| Benzene | 74.9% | | |
| ⌬—R | | | |
| (R = $C_1$-$C_7$) | | | |
| Olefins | — | | |

Offretite, much like the ZSM-5 and ZSM-12 zeolites of the previous examples, is shown to have desirable selectivity to reaction of the 2-phenyl isomer with only slight reaction of the 3-phenyloctane. Virtually none of the 4-phenyloctane has been reacted.

TABLE V

Example 6
Catalyst: Mordenite (—Al)
Temp.: 250° C.
Press.: Atm.
WHSV: 5

|  | Feed | Product | φ-C$_8$ Isomer Loss |
|---|---|---|---|
| 2-Phenyloctane | 11.7% | 1.7% | 85.5% |
| 3-Phenyloctane | 6.3% | 4.0% | 36.5% |
| 4-Phenyloctane | 5.1% | 4.6% | 9.8% |
| Benzene | 76.1% | 79.7% |  |
|  | — | 5.0% |  |

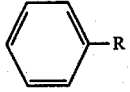

(R = C$_1$–C$_8$)
Olefins — 2.7%

TABLE VI

Example 7
Catalyst: Beta Zeolite
Temp.: 300° C.
Press.: Atm.
WHSV: 5

|  | Feed | Product | φ-C$_8$ Isomer Loss |
|---|---|---|---|
| 2-Phenyloctane | 10.8% | 3.3% | 69.4% |
| 3-Phenyloctane | 5.85% | 4.3% | 26.5% |
| 4-Phenyloctane | 4.8% | 4.2% | 12.5% |
| Benzene | 77.85% | 85.2% |  |
|  | — | 1% |  |

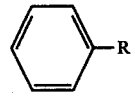

(R = C$_1$–C$_7$)
Olefins — 1.3%

TABLE VII

Example 8
Catalyst: SiO$_2$ . Al$_2$O$_3$
Temp.: 350° C.
Press.: Atm.
WHSV: 6

|  | Feed | Product | φ-C$_8$ Isomer Loss |
|---|---|---|---|
| 2-Phenyloctane | 11.4% | 2.6% | 77.2% |
| 3-Phenyloctane | 6.1% | 2.1% | 65.6% |
| 4-Phenyloctane | 5.0% | 2.0% | 60.0% |
| Benzene | 77.0% | 83.1% |  |
|  | — | 2.5% |  |

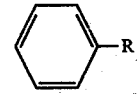

(R = C$_1$–C$_7$)
Olefins — 7.7%

As will be seen, the catalysts of Examples 6–8 were not appreciably selective toward the 2-phenyloctane. Table VIII below summarizes the selectivity of the tested catalysts using the ratio of the cracking rate constants k as an indicium of selectivity toward the 2-phenyloctane relative to the 3 and 4-phenyloctanes.

TABLE VIII

| Example | Catalyst | φ-C$_8$ Cracking Selectively $k_{(2)}/k_{(3+4)}$ |
|---|---|---|
| 2 | HZSM-5 | >350 |
| 3 | HZSM-5 (steamed) | >500 |
| 4 | HZSM-12 | 21 |
| 5 | Offretite | 22 |
| 6 | Mordenite (—Al) | 7 |
| 7 | Beta | 5 |
| 8 | SiO$_2$ . AlO$_3$ | 1.5 |

EXAMPLES 9–13

In the same manner as the foregoing examples, a sample of mixed phenyldodecanes in benzene was passed over various cracking catalysts at temperatures ranging between 200° C. and 300° C. The feed composition comprised:

| 2-Phenyldodecane | 9.74% |
|---|---|
| 3-Phenyldodecane | 5.32% |
| 4-Phenyldodecane | 4.09% |
| 5-Phenyldodecane | 4.16% |
| 6-Phenyldodecane | 3.95% |

Table IX below is a summary of the cracking activity of the catalysts, using the pseudo first order rates of cracking of the 2-isomer relative to the 3-isomer as a measure of the catalyst shape selectivity.

TABLE IX

| Example | Catalyst | 2-Phenyldodecane Reacted | $k_{(2)}/k_{(3)}$ |
|---|---|---|---|
| 9 | HZSM-5 | 99.0 | 400 |
| 10 | HZSM-5 (steamed) | 99.1% | ~400 |
| 11 | HZSM-12 | 94.5 | 8 |
| 12 | Offretite | 89 | 7 |
| 13 | Mordenite (—Al) | 94 | 4 |

The examples demonstrate the very high degree of shape selectivity of the most preferred catalyst (HZSM-5) as compared to a non-shape-selective catalyst (SiO$_2$-.Al$_2$O$_3$) and various partially shape-selective catalysts, including dealuminized mordenite which is outside the scope of this invention.

Although the foregoing examples will illustrate some preferred embodiments of the disclosed process, it is of course to be understood that numerous variations can be resorted to without departing from the spirit and scope of this invention, as those having skill in the art will readily appreciate.

What is claimed is:

1. A process for selective cracking of the 2-phenylalkane isomer contained in mixtures comprising said 2-phenylalkane isomer with other positional isomers of said phenylalkane; said process comprising contacting said isomeric mixture with a crystalline zeolite catalyst having a constraint index of about 1 to 12 and a silica to alumina ratio of at least about 12, said contacting being at a temperature of between about 150° C. and about 550° C. and at a pressure of between about $10^4$ N/m$^2$ and about $10^6$ N/m$^2$.

2. The process of claim 1 wherein said crystalline zeolite catalyst is chosen from the group consisting of ZSM-5, ZSM-11, ZSM-12, ZSM-23, ZSM-35, ZSM-38 and offretite.

3. A process as defined in claim 1 wherein the alkyl substituent of said 2-phenylalkane comprises from about 6 to about 20 carbon atoms in a linear chain.

4. A process as defined in claim 3 wherein said 2-phenylalkane is 2-phenyloctane.

5. A process as defined in claim 3 wherein said 2-phenylalkane is 2-phenyldodecane.

6. A process as defined in claim 1 wherein said temperature is between about 200° C. and about 400° C. and said pressure is between about $5 \times 10^4$ N/m$^2$ and $5 \times 10^5$ N/m$^2$.

7. A process as defined in claim 1 wherein said zeolite is ZSM-5.

8. A process as defined in claim 1 wherein said zeolite is ZSM-11.

9. A process as defined in claim 1 wherein said zeolite is ZSM-12.

10. A process as defined in claim 1 wherein said zeolite is ZSM-23.

11. A process as defined in claim 1 wherein said zeolite is ZSM-35.

12. A process as defined in claim 1 wherein said zeolite is ZSM-38.

13. A process as defined in claim 1 wherein said zeolite is offretite.

14. A process as defined in claim 1, 2, 7, 8, 9, 10, 11, 12 or 13 wherein said zeolite catalyst additionally comprises a binder therefor.

* * * * *

UNITED STATES PATENT AND TRADEMARK OFFICE
CERTIFICATE OF CORRECTION

PATENT NO. : 4,234,751

DATED : November 18, 1980

INVENTOR(S) : Lewis B. Young

It is certified that error appears in the above-identified patent and that said Letters Patent are hereby corrected as shown below:

Column 1, line 48, "2p-pheny-" should read --2-pheny- --.

Column 9, line 48, Line 3 of Table 1 was omitted; should read

|  | Feed | Product |
|---|---|---|
| --4-Phenyloctane | 5.0% | 5.0% |

*Signed and Sealed this*

*Third* Day of *March 1981*

[SEAL]

Attest:

RENE D. TEGTMEYER

*Attesting Officer*     *Acting Commissioner of Patents and Trademarks*